United States Patent
Clark et al.

(10) Patent No.: US 7,795,487 B2
(45) Date of Patent: Sep. 14, 2010

(54) PROCESS AND CATALYST FOR THE TRANSALKYLATION OF AROMATICS

(75) Inventors: Michael C. Clark, Chantilly, VA (US); Jane C. Cheng, Bridgewater, NJ (US); Ajit B. Dandekar, Bridgewater, NJ (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 392 days.

(21) Appl. No.: 11/886,045

(22) PCT Filed: Feb. 27, 2006

(86) PCT No.: PCT/US2006/006866

§ 371 (c)(1), (2), (4) Date: Sep. 10, 2007

(87) PCT Pub. No.: WO2006/107462

PCT Pub. Date: Oct. 12, 2006

(65) Prior Publication Data

US 2008/0167508 A1     Jul. 10, 2008

(51) Int. Cl.
*C07C 6/12* (2006.01)
*C07C 2/66* (2006.01)

(52) U.S. Cl. .................. 585/475; 585/467; 585/323

(58) Field of Classification Search ............... 585/475, 585/467, 323
See application file for complete search history.

(56) References Cited

U.S. PATENT DOCUMENTS

| | | |
|---|---|---|
| 3,962,364 A | 6/1976 | Young |
| 4,891,458 A | 1/1990 | Innes et al. |
| 4,992,606 A | 2/1991 | Kushnerick et al. |
| 5,081,323 A | 1/1992 | Innes et al. |
| 5,149,894 A | 9/1992 | Holtermann et al. |
| 5,334,795 A | 8/1994 | Chu et al. |
| 5,371,310 A | 12/1994 | Bennett et al. |
| 5,457,078 A | 10/1995 | Absil et al. |
| 5,470,810 A | 11/1995 | Degnan et al. |
| 5,557,024 A | 9/1996 | Cheng et al. |
| 5,658,454 A | 8/1997 | Absil et al. |
| 5,710,085 A | 1/1998 | Absil et al. |
| 5,833,840 A | 11/1998 | Absil et al. |
| 5,998,687 A | 12/1999 | Woodle et al. |
| 6,162,416 A | 12/2000 | Gajda et al. |
| 6,888,037 B2 * | 5/2005 | Dandekar et al. ........... 585/467 |
| 2003/0028060 A1 | 2/2003 | Dandekar et al. |
| 2003/0050521 A1 | 3/2003 | Dandekar et al. |
| 2003/0092949 A1 | 5/2003 | Dandekar et al. |
| 2004/0059167 A1 | 3/2004 | Clark et al. |
| 2004/0171899 A1 | 9/2004 | Pohl |

FOREIGN PATENT DOCUMENTS

| | | |
|---|---|---|
| EP | 0 220 933 | 5/1987 |
| EP | 0 439 632 | 8/1991 |
| EP | 0 467 007 | 1/1992 |
| EP | 0 719 750 | 7/1996 |
| EP | 0 949 227 | 10/1999 |
| RU | 2 097 129 | 11/1997 |
| WO | 98/14417 | 4/1998 |
| WO | 01/37994 | 5/2001 |
| WO | 02/08159 | 1/2002 |

OTHER PUBLICATIONS

Condensed Chemical Dictionary, Eighth Edition, Van Nostrand Reinhold Co., 1971, p. 881.

* cited by examiner

*Primary Examiner*—Thuan Dinh Dang
(74) *Attorney, Agent, or Firm*—D. M. Tyus

(57) ABSTRACT

Disclosed herein is a process and catalyst for producing a monoalkylated aromatic compound from a polyalkylated aromatic compound, comprising the step of contacting an alkylatable aromatic compound with a polyalkylated aromatic compound under at least partial liquid phase conditions in the presence of a zeolite beta catalyst having a phosphorus content in the range of 0.001 wt. % to 10.0 wt. % of said catalyst, to provide a product which comprises a monoalkylated aromatic compound.

5 Claims, No Drawings

PROCESS AND CATALYST FOR THE TRANSALKYLATION OF AROMATICS

CROSS REFERENCE TO RELATED APPLICATIONS

This application is a 35 U.S.C. 371 National Stage Application of International Application No. PCT/US2006/006866, filed Feb. 27, 2006, which claims the benefit of Provisional Application No. 60/666,808, filed Mar. 31, 2005, the disclosures of which are hereby incorporated by reference in their entireties.

BACKGROUND OF THE INVENTION

The present invention relates to a process and catalyst for the transalkylation of aromatics, particularly the transalkylation of polyisopropylbenzene with benzene to produce cumene and the transalkylation of polyethylbenzene with benzene to produce ethylbenzene. Ethylbenzene is a valuable commodity chemical and is used in the production of styrene monomer. Cumene (isopropylbenzene) is also a valuable commodity chemical and is used in the production of phenol and acetone.

Presently, ethylbenzene is often produced by a liquid phase alkylation process from benzene and ethylene in the presence of an alkylation catalyst. The liquid phase process operates at a lower temperature than its vapor phase counterpart and, therefore, produces a lower yield of polyalkylated by-products and other impurities. The alkylation of aromatic hydrocarbon compounds employing zeolite catalysts is known and understood in the art. U.S. Pat. No. 5,334,795 describes the liquid phase alkylation of benzene with ethylene in the presence of MCM-22 to produce ethylbenzene; and U.S. Pat. No. 4,891,458 discloses liquid phase alkylation and transalkylation process using zeolite beta.

Zeolite-based catalyst systems are used in the propylation of benzene to cumene. U.S. Pat. No. 4,992,606 discloses a process for preparing short chain alkyl aromatic compounds using MCM-22, including the liquid phase alkylation of benzene with propylene in the presence of MCM-22 to produce cumene.

Alkylation processes in commercial use for the production of ethylbenzene and cumene produce certain polyalkylated by-products in addition to ethylbenzene and cumene. It is well known in the art to transalkylate the polyalkylated by-products with benzene or other alkylatable aromatic to produce additional ethylbenzene or cumene. This transalkylation reaction may be accomplished by feeding the polyalkylated by-products through a transalkylation reactor operated under suitable conditions and in the presence of a transalkylation catalyst. Also, the polyalkylated by-products may be recycled to an alkylation reactor in the presence of an alkylation catalyst that is capable of performing the transalkylation reaction. U.S. Pat. No. 5,557,024 discloses a process for preparing short chain alkyl aromatic compounds using MCM-56 and the use of zeolite catalysts such as MCM-22, zeolite X, zeolite Y and zeolite beta for the transalkylation of the polyalkylated by-products.

Conducting the transalkylation reaction under liquid phase conditions imposes increased demands on the transalkylation catalyst. Heretofore, the transalkyation catalysts of the prior art have lacked desired activity or have not achieved adequate conversion rates for liquid phase transalkylation reactions.

U.S. Pat. No. 5,470,810 discloses that the addition of phosphorus to porous crystalline materials having the x-ray structure of MCM-22 improves the hydrothermal stability of the catalyst to maintain activity after repeated cycles of steaming as experienced in FCC processes.

U.S. Pat. No. 3,962,364 discloses that the addition of at least 0.5 wt. % phosphorus to a crystalline aluminosilicate zeolite, such as ZSM-5 to increase its selectivity for the desired alkylated hydrocarbon in the vapor phase alkylation of aromatic hydrocarbons.

U.S. Patent Publication 2003-0028060-A1 discloses the modification of alkylation catalyst, such as MCM-22, MCM-49 and MCM-56 with phosphorus to increase the activity and selectivity of the catalyst in the alkylation of aromatic compounds under liquid phase conditions.

However, none of these references contemplate a transalkylation catalyst that comprises zeolite beta catalyst that has been impregnated with phosphorus and exhibits unexpectedly higher relative catalytic activity as compared to conventional zeolite beta for use in alkylation and transalkylation processes.

SUMMARY OF THE INVENTION

According to the invention, there is provided a process for producing a monoalkylated aromatic compound from a polyalkylated aromatic compound, comprising the step of contacting an alkylatable aromatic compound with a polyalkylated aromatic compound under at least partial liquid phase conditions in the presence of a zeolite beta catalyst having a phosphorus content in the range of 0.001 wt. % to 10.0 wt. % of said catalyst, to provide a product which comprises a monoalkylated aromatic compound. Preferably, the catalytic activity of said zeolite beta catalyst is greater than the catalyst activity of a zeolite beta catalyst that is free of phosphorous when said first and second zeolite beta catalysts are compared under equivalent conditions.

Preferably, the beta zeolite transalkylation catalyst of step (b) is the Hydrogen-form of zeolite Beta and $Al_2O_3$ (Alumina 203) in a weight ratio of 80/20. More preferably, the beta zeolite has a X-ray diffraction pattern including d-spacing maxima at 11.4±0.2, 7.4±0.2, 6.7±0.2, 4.25±0.1, 3.97±0.1, 3.0±0.1, 2.2±0.1 Angstrom. The phosphorus content of the beta zeolite transalkylation catalyst is preferably in the range of 0.001 wt. % to 10.0 wt. % of said catalyst; more preferably the phosphorus content is from 0.005 wt. % to 3.0 wt. % of said catalyst; and most preferably the phosphorus content is in the range of 0.01 wt. % to 0.5 wt. % of said catalyst.

Preferably, the alkylating agent of step (a) is propylene or ethylene and the alkylatable aromatic compound is benzene.

Preferably, the polyalkylated compound of step (b) above is polyethylbenzene and the alkylatable compound is benzene to produce ethylbenzene as the monoalkylated aromatic product.

Preferably, the polyalkylated compound of step (b) above is polyisopropylbenzene and the alkylatable compound is benzene to produce cumene as the monoalkylated aromatic product.

DETAILED DESCRIPTION OF THE INVENTION

The present invention relates to a novel zeolite beta catalyst impregnated with phosphorus (P-Beta) that exhibits unexpectedly higher relative catalytic activity as compared to conventional zeolite beta. Preferably, the beta zeolite transalkylation catalyst of step (b) is the Hydrogen-form of zeolite Beta and $Al_2O_3$ (Alumina 203) in a weight ratio of 80/20. More preferably, the P-Beta catalyst has an X-ray diffraction pattern including d-spacing maxima at 11.4±0.2, 7.4±0.2, 6.7±0.2, 4.25±0.1, 3.97±0.1, 3.0±0.1, 2.2±0.1 Angstrom and contains phosphorus. Preferably, the phosphorus content of P-Beta is in the range of 0.001 wt. % to 10.0 wt. % of said catalyst; more preferably, such phosphorus content is in the range of 0.005 wt. % to 3.0 wt. % of said catalyst; and most preferably such phosphorus content is in the range of 0.01 wt. % to 0.5 wt. % of said catalyst.

The invention also relates to a process for producing a monoalkylated aromatic compound wherein an alkylation step, carried out under at least partial liquid phase conditions, an alkylatable compound is reacted with an alkylating agent, to produce a monoalkylated aromatic end product as well as a polyalkylated compound, which is separated and fed to a transalkylation process step. In the transalkylation step, which is also preferably conducted under at least partial liquid phase conditions, the polyalkylated end product is contacted in a transalkylation reactor with a alkylatable aromatic compound preferably in the presence of the P-Beta catalyst to produce a monoalkylated compound. More preferably, the P-Beta catalyst has an X-ray diffraction pattern including d-spacing maxima at 11.4±0.2, 7.4±0.2, 4.25±0.1, 3.97±0.1, 3.0±0.1, 2.2±0.1 Angstrom and contains phosphorous. Preferably, the phosphorus content of P-Beta is in the range of 0.001 wt. % to 10.0 wt. % of said catalyst; more preferably, such phosphorus content is in the range of 0.005 wt. % to 3.0 wt. % of said catalyst; and most preferably such phosphorus content is in the range of 0.01 wt. % to 0.5 wt. % of said catalyst.

The term "aromatic" when used in reference to the alkylatable compounds which are useful herein is to be understood in accordance with its art-recognized scope which includes alkyl-substituted and unsubstituted mono- and polynuclear compounds. Compounds of an aromatic character that possess a heteroatom are also useful provided they do not act as catalyst poisons under the reaction conditions selected.

Substituted aromatic compounds that may be alkylated in accordance with the present invention, such as alkylatable aromatic compounds, must possess at least one hydrogen atom directly bonded to the aromatic nucleus. The aromatic rings can be substituted with one or more alkyl, aryl, alkylaryl, alkoxy, aryloxy, cycloalkyl, halide, and/or other groups that do not interfere with the alkylation reaction.

Suitable aromatic hydrocarbons include benzene, naphthalene, anthracene, naphthacene, perylene, coronene, and phenanthrene, with benzene being preferred.

Generally the alkyl groups which can be present as substituents on the aromatic compound contain from 1 to about 22 carbon atoms and usually from about 1 to 8 carbon atoms, and most usually from about 1 to 4 carbon atoms.

Suitable alkyl substituted aromatic compounds, such as alkylating agents, include toluene, xylene, isopropylbenzene, normal propylbenzene (n-propylbenzene), alpha-methylnaphthalene, ethylbenzene, mesitylene, durene, cymenes, butylbenzene, pseudocumene, o-diethylbenzene, m-diethylbenzene, p-diethylbenzene, isoamylbenzene, isohexylbenzene, pentaethylbenzene, pentamethylbenzene; 1,2,3,4-tetraethylbenzene; 1,2,3,5-tetramethylbenzene, 1,2,4-triethylbenzne; 1,2,3-trimethylbenzene, m-butyltoluene; p-butyltoluene; 3,5-diethyltoluene; o-ethyltoluene; p-ethyltoluene; m-propyltoluene; 4-ethyl-m-xylene; dimethylnaphthalenes; ethylnaphthalene; 2,3-dimethylanthracene; 9-ethylanthracene; 2-methylanthracene; o-methylanthracene; 9,10-dimethylphenanthrene; and 3-methyl-phenathrene. Higher molecular weight alkylaromatic hydrocarbons can also be used as starting materials and include aromatic hydrocarbons such as are produced by the alkylation of aromatic hydrocarbons with olefin oligomers. Such products are frequently referred to in the art as alkylate and include hexylbenzene, nonylbenzene, dodecylbenzene, pentadecylbenzene, hexyltoluene, nonyltoluene, dodecyltoluene, pentadecytoluene, etc. Very often alkylate is obtained as a high boiling fraction in which the alkyl group attached to the aromatic nucleus varies in size from about $C_6$ to about $C_{12}$. When cumene or ethylbenzene is the desired product, the present process produces acceptably little by-products such as xylenes. The xylenes make in such instances may be less than about 500 ppm.

Reformate containing substantial quantities of benzene, toluene and/or xylene constitutes a particularly useful feed for the alkylation process of this invention.

The alkylating agents that may be useful in the process of this invention generally include any aliphatic or aromatic organic compounds having one or more available alkylating aliphatic groups capable of reaction with the alkylatable aromatic compound.

Preferably, the alkylating agent employed herein has at least one alkylating aliphatic group possessing from 1 to 5 carbon atoms. Examples of such alkylating agents are olefins such as ethylene, propylene, the butenes, and the pentenes; alcohols (inclusive of monoalcohols, dialcohols and trialcohols) such as methanol, ethanol, the propanols, the butanols, and the pentanols; aldehydes such as formaldehyde, acetadehyde, propionaldehyde, butyraldehyde, and n-valeraldehyde; and alkyl halides such as methyl chloride, ethyl chloride, the propyl chlorides, the butyl chlorides and the pentyl chlorides.

Mixtures of light olefins are especially useful as alkylating agents in the alkylation process of this invention. Accordingly, mixtures of ethylene, propylene, butenes, and/or pentenes which are major constituents of a variety of refinery streams, e.g., fuel gas, gas plant off-gas containing ethylene, propylene, etc., naphtha cracker off-gas containing light olefins and refinery FCC propane/propylene streams, are useful are useful alkylating agents herein. For example, a typical FCC light olefin stream possesses the following composition:

|  | Wt. % | Mole % |
| --- | --- | --- |
| Ethane | 3.3 | 5.1 |
| Ethylene | 0.7 | 1.2 |
| Propane | 4.5 | 15.3 |
| Propylene | 42.5 | 46.8 |
| Isobutane | 12.9 | 10.3 |
| n-Butane | 3.3 | 2.6 |
| Butenes | 22.1 | 18.32 |
| Pentanes | 0.7 | 0.4 |

Reaction products which may be obtained from the process of the invention include ethylbenzene from the reaction of benzene with ethylene, cumene from the reaction of benzene with propylene, ethyltoluene from the reaction of toluene with ethylene, cymenes from the reaction of toluene with propylene, and sec-butylbenzene from the reaction of benzene and n-butenes. Preferably, the process of the invention relates to the production of ethylbenzene by the alkylation of benzene with ethylene followed by the transalkylation of the diethylbenezene by-products with additional benzene; the production of cumene by the alkylation of benzene with propylene followed by the transalkylation of the diisopropylbenzene by-products with additional benzene.

In one embodiment of the invention, the alkylation process of this invention is conducted such that the organic reactants, i.e., the alkylatable aromatic compound and the alkylating agent, are brought into contact with an alkylation or transalkylation catalyst in a suitable alkylation or transalkylation reaction zone such as, for example, in a flow reactor containing a fixed bed of the catalyst composition, under effective alkylation conditions. Such conditions include a temperature of from about 32° F. to about 932° F. (0° C. to 500° C.), and preferably between about 122° F. and about 452° F. (50° C. to 250° C.), a pressure of from about 0.2 to about 250 atmospheres (20-25,000 kPa), and preferably from about 5 to about 100 atmospheres (500-10,000 kPa), a molar ratio of alkylatable aromatic compound to alkylating agent of from about 0.1:1 to about 50:1, and preferably can be from about 0.5:1 to about 10:1, and a feed weight hourly space velocity (WHSV) of between about 0.1 and 500 $hr^{-1}$, preferably between 0.5 and 100 $hr^{-1}$.

The reactants can be in either in the vapor phase or partially or completely in the liquid phase and can be neat, i.e., free from intentional admixture or dilution with other material, or they can be brought into contact with the zeolite catalyst composition with the aid of carrier gases or diluents such as, for example, hydrogen and nitrogen.

In another embodiment of the invention, when benzene is alkylated with ethylene to produce an alkylation reactor effluent that contains ethylbenzene. The alkylation reaction may be carried out in the liquid phase or in at least partial liquid phase under conditions including a temperature between 300° F. and 600° F. (about 150° C. to 316° C.), more preferably between 400° F. and 500° F. (about 205° C. and 260° C.), a pressure up to about 3000 psig (20865 kPa), more preferably between 400 and 800 psig (2869 and 5600 kPa), a weight hourly space velocity (WHSV) between about 0.1 and 20 $hr^{-1}$, more preferably between 0.5 $hr^{-1}$ and 6 $hr^{-1}$, based on the ethylene feed, and a ratio of the benzene to the ethylene in the alkylation reactor from 1:1 to 30:1 molar, more preferably from about 1:1 to 10:1 molar.

In still another embodiment of the invention, when benzene is alkylated with propylene to produce an alkylation reactor effluent that contains cumene. The alkylation reaction may be carried out in the liquid phase or in at least partial liquid phase under conditions including a temperature of up to about 482° F. (250° C.), e.g., up to about 302° F. (150° C.), e.g., from about 50° F. to about 257° F. (10° C. to 125° C.); a pressure of about 250 atmospheres (25,000 kPa) or less, e.g., from about 1 to about 30 atmospheres (100 kPa-3000 kPa); and an aromatic hydrocarbon weight hourly space velocity 5 $hr^{-1}$ to about 250 $hr^{-1}$, preferably from 5 $hr^{-1}$ to 50 $hr^{-1}$.

The term "at least partial liquid phase" when used in connection with a reaction mixture in contact with a solid catalyst means that such reaction mixture includes all liquid phase components or mixed-phase components.

The term "mixed-phase" when used in connection with a reaction mixture means that such mixture includes liquid phase components and vapor phase components.

The alkylation catalyst that may be useful in this invention is a crystalline molecular sieve preferably selected from MCM-22 (described in detail in U.S. Pat. No. 4,954,325), MCM-36 (described in detail in U.S. Pat. No. 5,250,277), MCM-49 (described in detail in U.S. Pat. No. 5,236,575), MCM-56 (described in U.S. Pat. No. 5,362,697), and zeolite beta (described in detail in U.S. Pat. No. 3,308,069). The molecular sieve can be combined in conventional manner with an oxide binder, such as $Al_2O_3$ (Alumina 203), or can be self bound such that the final alkylation catalyst contains between 2 and 100 wt. % sieve.

The alkylation reactor effluent contains the excess aromatic feed, monoalkylated aromatic compounds (such as ethylbenzene or cumene), polyalkylated aromatic compounds (such as polyethylbenzene or polyisopropylbenzene), and various impurities. The aromatic feed is recovered by distillation and recycled to the alkylation reactor. Usually a small bleed is taken from the recycle stream to eliminate unreactive impurities from the loop. The bottoms from the benzene distillation are further distilled to separate monoalkylated product from polyalkylated products and other heavies.

The term "polyethylbenzene" (PEB) in reference to the polyalkylated aromatic compounds which are useful herein is to be understood in accordance with its art-recognized scope which includes, by way of illustration and not limitation, diethylbenzene (DEB) and triethylbenzene (TEB).

The term "polyisopropylbenzene" (PIPB) in reference to polyalkylated aromatic compounds which are useful herein is to be understood in accordance with its art-recognized scope which includes, by way of illustration and not limitation, diisopropylbenzene (DIPB) and triisopropylbenzene (TIPB).

The polyalkylated products separated from the alkylation reactor effluent are reacted with additional aromatic feed in a transalkylation reactor, which may or may not be separated from the alkylation reactor, over a suitable transalkylation catalyst. Preferably, the transalkylation catalyst is P-Beta. More preferably, the P-Beta catalyst has an X-ray diffraction pattern including d-spacing maxima at 11.4±0.2, 7.4±0.2, 6.7±0.2, 4.25±0.1, 3.97±0.1, 3.0±0.1, 2.2±0.1 Angstrom and contains phosphorus. Preferably, the phosphorus content of P-Beta is in the range of 0.001 wt. % to 10.0 wt. % of said catalyst; more preferably, such phosphorus content is in the range of 0.005 wt. % to 3.0 wt. % of said catalyst; and most preferably such phosphorus content is in the range of 0.01 wt. % to 0.5 wt. % of said catalyst.

To prepare one embodiment of the P-Beta transalkylation catalyst of this invention, 50 grams of a zeolite beta catalyst comprising 80 wt. % of hydrogen form (H-form) of beta zeolite crystal and 20 wt. % alumina ($Al_2O_3$) 1/20" (1.27 mm) quadrulobe extrudates were impregnated to incipient wetness with an aqueous solution of ammonium hydrogen phosphate, 0.43 grams of ammonium hydrate phosphate dissolved in 30 cc of distilled water. The P-Beta catalyst was then calcined at 1000° F. (538° C.) with a 10 hour hold at full air. The P-Beta catalyst was then dried off-line at 200° C. at atmospheric pressure with 100 cc/min flowing $N_2$ for 2 hours. Two grams of the P-Beta (1/20" [1.59 mm] diameter quadrulobe extrudates chopped to 1/16" [1.59 mm] length) was used. The phosphorus content of the P-Beta transalkylation catalyst was 0.2 wt. %. The amount of phosphorus on the final catalyst can be varied by increasing or decreasing the concentration of phosphorus in the initial aqueous solution used in impregnation, or by depositing phosphorus by ion exchange and varying the time and temperature of the process, or by other methods known to those skilled in the art.

The transalkylation reaction of the invention is conducted under at least partial liquid phase conditions such that the polyalkylated aromatics react with additional alkylatable aromatic compounds to produce additional monoalkylated product. Suitable transalkylation conditions include a temperature of 212° F. to 500° F. (100° C. to 260° C.), a pressure of 10 to 50 barg (1100-5100 kPa), a WHSV 1 $hr^{-1}$ to 10 $hr^{-1}$ based on total feed, and benzene/polyalkylated benzene weight ratio 1:1 to 6:1.

When the polyalkylated aromatics are polyisopropylbenzenes and are contacted with benzene to produce cumene in a transalkylation reactor, the transalkylation conditions preferably include a temperature 50° F. to about 100° F. (100° C. to 200° C.), a pressure of 20 to 30 barg (2100-3100 kPa), weight hourly space velocity of 10 to 72 on total feed and benzene/PIPB weight ratio 1:1 to 6:1.

When the polyalkylated aromatics are polyethylbenzenes and are contacted with benzene to produce ethylbenzene in a transalkylation reactor, the transalkylation conditions preferably include a temperature of 428° F. to about 500° F. (220 to 260° C.), a pressure of 20 to 30 barg (2100-3100 kPa), weight hourly space velocity of 2 to 6 on total feed and benzene/PEB weight ratio 2:1 to 6:1.

The effluent from the transalkylation reactor is blended with alkylation reactor effluent and the combined stream distilled to separate the desired monoalkylated product.

Embodiments of the present invention will be described in the following examples.

The transalkylation feed used in Examples 1 and 2 that follow were prepared as follows. Chemical grade benzene and para- and meta-diisopropylbenzene were purified by percolation over activated alumina. The purified diisopropylbenzenes were mixed 2:1 by weight (para:meta). The purified benzene and polyisopropylbenzenes were mixed 2:1 weight ratio and stored under nitrogen. A gas chromatograph (GC) analysis of the feed provided the composition by weight shown in Table I.

TABLE 1

| | |
|---|---|
| Methane | 0.005 |
| trans-2-Pentene | 0.034 |
| Other $C_6$ Paraffins | 0.004 |
| Benzene | 66.449 |
| Other $C_7$ Paraffins | 0.022 |
| Other $C_8$ Paraffins | 0.008 |
| ortho-xylene | 0.001 |
| Cumene | 0.028 |
| Other $C_{10}$ Paraffins | 0.003 |
| 1,2-diethylbenzene | 0.044 |
| Other $C_{10}$ Aromatics | 0.002 |
| Other $C_{11}$ Aromatics | 0.435 |
| 1,3-diisopropylbenzene | 11.776 |
| 1,4-diisopropylbenzene | 21.183 |
| 1,2,4-tetraethylbenzene | 0.001 |
| 1,2,3-tetraethylbenzene | 0.002 |
| Sum | 99.997 |

Example 1

Cumene Synthesis Via Benzene/PIPB Transalkylation Over Zeolite Beta Catalyst

Two grams of a zeolite beta catalyst comprising 80 wt. % of hydrogen form (H-form) of beta zeolite crystal and 20 wt. % alumina ($Al_2O_3$) cylindrical extrudates (chopped to 1/16" [1.59 mm] length) was used for transalkylation of the feed described in Table 1. The zeolite beta catalyst was dried off-line at 392° F. (200° C.) at atmospheric pressure (100 kPa) with 100 cc/min flowing $N_2$ for 2 hours. The zeolite beta catalyst was diluted with approximately 2.6 grams of sand per gram of catalyst and charged to an isothermal, down-flow, 3/8" [9.5" mm] outside diameter fixed bed reactor. The reactor was heated to 356° F. (180° C.) under flowing nitrogen. The feed described in Table 1 was introduced into the reactor (based on total catalyst weight) and the reactor pressure was set to 300 psig (2170 kPa) by a grove loader. Weight hourly space velocity (WHSV) was set to achieve approximately 50% total DIPB conversion. The beta zeolite reached approximately 50% DIPB conversion at 16 WHSV. After lining out weight hourly space velocity, the total product was vaporized and sent to an on-line HP 5890 GPC. Relative activity based on a first order reaction rate constant, cumene selectivity and impurity-make for the catalyst were determined and are shown in Table 2.

Example 2

Cumene Synthesis Via Benzene/PIPB Transalkylation Over P-Beta Catalyst

To prepare the P-Beta catalyst, 50 grams of sample comprising 80 wt. % of hydrogen form (H-form) beta zeolite crystal and 20 wt. % alumina ($Al_2O_3$ 1/20" (1.27 mm) quadrulobe extrudate was impregnated to incipient wetness with an aqueous solution of ammonium hydrogen phosphate prepared by dissolving 0.43 grams of ammonium hydrate phosphate in 30 cc of distilled water. The P-Beta was then calcined at 1000° F. (538° C.) with a 10 hour hold at full air. The P-Beta was then dried off-line at 392° F. (200° C.) at atmospheric pressure (100 kPa) with 100 cc/min flowing $N_2$ for 2 hours. The total phosphorus content of the catalyst was 0.02 wt. % based on the total weight of the catalyst. Two (2.0) grams of the P-Beta extrudates (chopped to 1/16" [1.59 mm] length) were used for transalkylation of the feed described in Table 1. The P-Beta was diluted with approximately 2.6 grams of sand per gram of catalyst and charged to an isothermal, down-flow, 3/8" [9.5 mm] outside diameter fixed bed reactor. The reactor was heated to 356° F. (180° C.) under flowing nitrogen. The feed described in Table 1, was introduced into the reactor (based on total catalyst weight) and reactor pressure was set to 300 psig (2170 kPa) by a grove loader. Weight hourly space velocity (WHSV) was set to achieve approximately 50% total DIPB conversion. P-Beta reached approximately 50% DIPB conversion at 72 WHSV. After lining out WHSV, the total product was vaporized and sent to an on-line HP 5890 GPC. Relative activity based on a first order reaction rate constant, cumene selectivity and impurity-make for the catalyst were determined and are also shown in Table 2.

TABLE 2

| | Zeolite-Beta | P-Beta |
|---|---|---|
| WHSV | 16 | 72 |
| Overall DIPB conversion | 49.0% | 53.9% |
| meta-DIPB conversion | 8.4% | 16.8% |
| para-DIPB conversion | 72.0% | 74.8% |
| Cumene Selectivity | 96.6% | 98.9% |
| N-propylbenzene/Cumene (ppmw) | 280 | 320 |
| Ethylbenzene/Cumene (ppmw) | 330 | 830 |
| Relative Activity | 16.1 | 83.2 |

The transalkylation feed used in Example 3 was prepared as follows. Chemical grade benzene was percolated through activated alumina. A polyethylbenzene (PEB) mixture containing 90% diethylbenzene (DEB) was obtained from a PEB column overhead of a commercial ethylbenzene unit, and percolated through activated alumina. Percolated benzene and PEB were mixed in a 3:1 weight ratio. A GC analysis of this feed provided the composition by weight shown in Table 3.

TABLE 3

| | Weight Percent |
|---|---|
| Benzene | 74.719 |
| Toluene | 0.021 |
| EB | 0.122 |
| n-propylbenzene | 0.005 |

TABLE 3-continued

| | Weight Percent |
|---|---|
| Ethyltoluene | 0.004 |
| Butylbenzene | 0.142 |
| meta-diethylbenzene | 13.235 |
| para-diethylbenzene | 5.500 |
| ortho-diethylbenzene | 4.518 |
| Triethylbenzene (TEB) | 1.601 |
| Others | 0.134 |
| Sum | 100.00 |

Example 3

Ethylbenzene Synthesis Via Benzene/PEB-Transalkylation Over Zeolite Beta Catalyst The transalkylation process was conducted with a down flow fixed-bed reactor which consisted of a three-zone furnace and a ⅜" (9.59 mm) outside diameter reactor with ⅛" (3.19 mm) outside diameter, central thermowall in the catalyst bed.

A sample of 0.5 grams of zeolite beta catalyst, comprising 65 wt. % hydrogen form of zeolite beta crystal and 35 wt. % alumina ($Al_2O_3$) binder, ¹⁄₁₆" (1.59 mm) cylindrical extrudate (chopped to ¹⁄₁₆" [1.59 mm] length) was diluted to 3 cc with sand and dried at 257° F. (125° C.) at atmospheric pressure (100 kPa) with 100 cc/min. flowing of $N_2$ for 2 hours. The $N_2$ was turned off and the grove loader was set to 500 psig (3616 kPa). The transalkylation feed described in Table 3 was introduced by an Isco pump at 257° F. (125° C.) and 60 cc/hr for 1 hour and then at 5 total WHSV. The reactor was ramped at 41° F./min. (5° C./min.) to 464° F. (240° C.) and then at 37° F./min. (3° C./min.) to 500° F. (260° C.). The product was collected in a cold trap and analyzed off-line on the HP 5890 GC equipped with a DB-1 capillary column. Catalysts were tested at 500° F. (260° C., 500 psig (3616 kPa), 3:1 benzene/PEB weight ratio with total flow rate as a variable. Relative activity based on a first order reaction rate constant, ethylbenzene selectivity and impurity-make for the catalysts were determined and are shown in Table 4.

TABLE 4

| | Zeolite Beta |
|---|---|
| WHSV | 10 |
| Overall DEB conversion | 50.3% |
| Butylbenzene conversion | 30.5% |
| TEB conversion | 18.3% |
| Selectivity, wt. % | |
| Lights | 0.207% |
| Toluene | 0.047% |
| Ethylbenzene | 98.073% |
| Cumene | 0.054% |
| n-propylbenzene | 0.038% |
| Ethyltoluene | 0.032% |
| Diphenylethanes | 0.856% |
| Others | 0.693% |
| Relative Activity | 7.7 |

The transalkylation feed used in Example 1 was prepared as follows. Chemical grade benzene was percolated through activated alumina column. A PEB mixture containing 69.4 wt. % DEB and 28.6 wt. % TEB was obtained from a PEB column overhead of a commercial ethylbenzene unit, and percolated through an activated alumina column. Percolated benzene and PEB were mixed in a 2:1 weight ratio. A GC analysis of this feed provided the composition by weight as shown in Table 5.

TABLE 5

| | Weight Percent |
|---|---|
| Lights | 0.015 |
| Benzene | 66.634 |
| Toluene | 0.013 |
| EB | 0.018 |
| Cumene | 0.016 |
| n-Propylbenzene | 0.023 |
| Ethyltoluene | 0.058 |
| Butylbenzene | 0.084 |
| meta-diethylbenzene | 14.550 |
| para-diethylbenzene | 6.722 |
| ortho-diethylbenzene | 1.788 |
| 1,3,5-tetraethylbenzene | 6.978 |
| 1,2,4-tetraethylbenzene | 2.521 |
| 1,2,3-tetraethylbenzene | 0.065 |
| Others | 0.516 |
| Sum | 100.001 |

Example 4

Ethylbenzene Synthesis Via Benzene/PEB Transalkylation Over P-Beta Catalyst

The transalkylation process was conducted with a down flow fixed-bed reactor which consisted of a three-zone furnace and a ⅜" (9.59 mm) outside diameter reactor with ⅛" (3.19 mm) outside diameter, central thermowall in the catalyst bed.

One-half gram of P-beta, a ¹⁄₂₀" (1.27 mm) quadrulobe extrudate (chopped to ¹⁄₁₆" [1.59 mm] length) containing 0.2 wt. % phosphates and 20% wt. alumina ($Al_2O_3$) binder was diluted to 3 cc with sand and dried at 257° F. (125° C.) and atmospheric pressure (100 kPa) with 100 cc/min of flowing $N_2$ for 2 hr. $N_2$ was turned off and the grove loader was set to 500 psig (3616 kPa). The feed, as described in Table 5 was introduced by an Isco pump at 257° F. (125° C.) and 60 cc/hr for 1 hour and then at 5 total WHSV. The reactor was ramped at 5° C./min to 240° C. The product was collected in a cold trap and analyzed off-line on a HP 5890 GC equipped with a DB-1 capillary column. Catalysts were tested at 464° F. (240° C.), 500 psig (3616 kPa), 2:1 benzene/PEB weight ratio with a total flow rate as a variable. Relative activity based on a first order reaction rate constant, ethylbenzene selectivity and impurity make for the catalysts were determined and are shown in Table 6.

TABLE 6

| | P-Beta |
|---|---|
| WHSV | 10 |
| Overall DEB conversion | 40.7% |
| Butylbenzene conversion | 12.0% |
| TEB conversion | 13.5% |
| Selectivity, wt. % | |
| Lights | 0.297% |
| Toluene | 0.043% |
| Ethylbenzene | 98.591% |
| Cumene | 0.010% |
| n-propylbenzene | 0.000% |
| Ethyltoluene | 0.000% |

TABLE 6-continued

|  | P-Beta |
| --- | --- |
| Diphenylethanes | 1.043% |
| Others | 0.016 |
| Relative Activity | 25.1 |

When the relative activity values for the catalysts are compared, P-beta is 5.1 times more active than conventional zeolite beta not comprising phosphorous in the transalkylation of cumene under equivalent conditions of WHSV; and 3.2 times more active than conventional zeolite beta in the transalkylation of ethylbenzene not comprising phosphorous under equivalent conditions of temperature, pressure and DIPB conversion.

While the present invention has been described and illustrated by reference to the preferred embodiments, those of ordinary skill in the art will appreciate that the invention lends itself to alternative embodiments not necessarily illustrated herein. For this reason, reference should be made solely to the appended claims for purposes of determining the true scope of the present invention.

The invention claimed is:

1. A process for producing cumene from a polyisopropylbenzene feed and a benzene feed, comprising the step of contacting said benzene feed with said polyisopropylbenzene feed under at least partial liquid phase conditions in the presence of a first transalkylation catalyst having a first catalytic activity, said first transalkylation catalyst comprising zeolite beta, alumina binder, and phosphorous, wherein the phosphorus content of said transalkylation catalyst is in the range of 0.01 wt. % to 0.5 wt. % of said first transalkylation catalyst, to provide a product which comprises cumene.

2. The process of claim 1, wherein said first catalytic activity is greater than a second catalyst activity of a second transalkylation catalyst which comprises zeolite beta and free of phosphorous, when said first and second transalkylation catalysts are compared under equivalent conditions.

3. The process of claim 1, further comprising the step of contacting an alkylatable aromatic compound with an alkylating agent under at least partial liquid phase conditions in the presence of an alkylation catalyst selected from the group consisting of MCM-22, MCM-36, MCM-49 and MCM-56, to provide an alkylation product comprising said polyisopropylbenzene feed.

4. The process of claim 1, wherein said first transalkylation catalyst is shaped in a form of a quadrulobe.

5. The process of claim 3, wherein said alkylatable aromatic compound is benzene and said alkylating agent is ethylene or propylene.

* * * * *